United States Patent
Frey et al.

(10) Patent No.: US 9,597,035 B2
(45) Date of Patent: Mar. 21, 2017

(54) SKIN-MOUNTABLE MEDICAL DEVICE

(71) Applicant: Roche Diabetes Care, Inc., Indianapolis, IN (US)

(72) Inventors: Stephan-Michael Frey, Pfungstadt (DE); Oliver Kube, Worms (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/938,001

(22) Filed: Nov. 11, 2015

(65) Prior Publication Data
US 2016/0135747 A1 May 19, 2016

(30) Foreign Application Priority Data

Nov. 14, 2014 (EP) ..................... 14193332

(51) Int. Cl.
| A61B 5/00 | (2006.01) |
| A61M 5/142 | (2006.01) |
| A61B 5/145 | (2006.01) |
| A61N 1/04 | (2006.01) |

(52) U.S. Cl.
CPC ........ *A61B 5/6833* (2013.01); *A61B 5/14532* (2013.01); *A61M 5/14248* (2013.01); *A61N 1/0496* (2013.01); *A61B 2560/04* (2013.01); *A61M 2205/586* (2013.01); *Y10T 428/14* (2015.01); *Y10T 428/149* (2015.01); *Y10T 428/1495* (2015.01)

(58) Field of Classification Search
CPC . A61B 5/6833; A61B 5/04087; A61B 5/6832; A61B 5/04085; A61B 2560/0468; A61B 2560/0406; A61B 5/14532; A61B 2560/04; Y10T 156/10; Y10T 428/14; Y10T 428/149; Y10T 428/1495; A61M 5/14248; A61M 2205/586; A61N 1/0496
See application file for complete search history.

(56) References Cited

U.S. PATENT DOCUMENTS

| 2011/0279963 A1 | 11/2011 | Kumar et al. |
| 2012/0035447 A1 | 2/2012 | Frey et al. |
| 2012/0071742 A1 | 3/2012 | Medina et al. |
| 2014/0012094 A1 | 1/2014 | Das et al. |
| 2014/0275932 A1 | 9/2014 | Zadig |

FOREIGN PATENT DOCUMENTS

EP 2 415 395 A1 2/2012

OTHER PUBLICATIONS

European Patent Application 14193332.5 Extended Search Report mailed May 28, 2015.

*Primary Examiner* — Patricia L Nordmeyer
(74) *Attorney, Agent, or Firm* — Woodard Emhardt Moriarty McNett and Henry LLP

(57) ABSTRACT

The invention concerns a skin-mountable medical device comprising a patch portion with a contact surface facing the skin of a patient during use, a process unit attached to the patch portion, and a plaster kit for securing the patch portion to the skin, wherein the plaster kit has a primary pad adapted to releasably adhere to at least a section of a peripheral skin surface surrounding the contact surface. According to the invention, the plaster kit further comprises at least one auxiliary pad which is connectable or connected to the patch portion and adapted to functionally replace the primary pad after a wearing time.

17 Claims, 3 Drawing Sheets

SKIN-MOUNTABLE MEDICAL DEVICE

CROSS-REFERENCE TO RELATED APPLICATION

This application claims the benefit of European Application No. 14 193 332.5, filed Nov. 14, 2014, the entire disclosure of which is hereby incorporated by reference.

BACKGROUND

The invention relates to a skin-mountable medical device comprising a patch portion with a contact surface facing the skin of a patient during use, a process unit particularly formed by a sensor or medication delivery set attached to the patch portion, and a plaster kit for securing the patch portion to the skin, wherein the plaster kit has a primary pad adapted to releasably adhere to at least a section of a peripheral skin surface surrounding the contact surface.

In the area of medical technology and specifically in the field of continuous glucose monitoring (CGM), a similar assembly is proposed in EP 2 415 395 A1. This document discloses an implantable sensor device in connection with a disposable body-mount fixed to the body by means of a plaster. In this connection a wearing period of at least several days is intended. Due to the implanted sensor, it should be avoided that the carrier plaster and hence the body-mount inadvertently detaches from the body.

SUMMARY

On this basis the object of the invention is to further improve the known devices and to achieve an improved efficiency for reliable, long-term use and at the same time uncomplicated handling.

The combination of features stated in claim 1 is proposed to achieve this object. Advantageous embodiments and further developments of the invention are derived from the dependent claims.

The invention is based on the idea of providing a plaster kit including exchangeable elements while keeping the patch portion fixed at the application site. Correspondingly, it is proposed according to the invention that the plaster kit further comprises at least one auxiliary pad which is connectable or connected to the patch and adapted to replace the primary pad after a wearing time. By use of such an auxiliary pad, it is possible to take account of physiological skin processes such as dissolution of skin particles and hair growth which could lead to detachment of the device after an initial wearing time. Moreover, the detached primary pad takes away the repelled skin layer, such that the auxiliary pad can be placed on freshly exposed skin with enhanced adhesiveness. The auxiliary or replacement pad can be applied on the periphery of the contact surface of the patch without lifting or displacement of the device and thus maintaining the application site unvaried.

A preferred embodiment provides that the primary pad and the at least one auxiliary pad are lying upon each other in a layered configuration. In this way, the auxiliary pad is always available and can be applied on demand without getting lost.

A further improvement provides that the auxiliary pad is bendably connected to a rim of the patch portion and forms a flap to uncover the primary pad for removal. In this way it is possible to further simplify the handling during detachment of the primary pad.

Advantageously, an adhesive coating of the auxiliary pad is separated by a liner from the primary pad in order to avoid interference when detaching the primary pad and to provide a fresh adhesive surface.

For carrying a process unit independently of the primary and auxiliary pads, it is advantageous when the plaster kit further comprises a base pad fixedly connected to the contact surface of the patch portion. It is also conceivable that the contact surface is formed by an adhesive coating for direct skin contact.

For further handling improvement it is advantageous when the primary pad is delimited by a tear-off perforation which allows detachment while keeping the patch portion in place.

Another advantageous embodiment provides that the auxiliary pad is formed as a separate ring which can be applied over the periphery of the patch portion. In this way, fixation of the device can be renewed with fresh plaster material which has not been carried on the body before.

In order to provide a mechanically stable connection it is advantageous when the plaster kit comprises a ring-shaped frame which is carried on the inner edge of an annular auxiliary pad, wherein the frame can be engaged to the patch portion preferably in a form-locking manner.

In another preferred embodiment there is provided a stack of at least two auxiliary pads which are joined together in a parallel folding pattern particularly in a Leporello-like fashion for sequential unfolding into a use position. In this way, it is possible to prolong the use period by a sequence of multiple replacements.

For further handling improvement it is advantageous when the auxiliary pads each are formed as a half-ring adapted to be turned over into a functional position adhering to the skin.

In order to avoid impairment of the device function during the entire use period, it is favorable when the patch portion remains affixed to the skin while the primary pad is replaced.

Advantageously, the primary pad has a tear-off section which can be separated from the skin independently of a remaining section of the primary pad which holds the device intermittently in place.

In a specific embodiment, the tear-off section is connected by means of a pull linkage to a remaining section of the primary pad, such that separation is possible without undue effort for the patient.

Another advantageous embodiment provides that the primary pad comprises several separate sections in a mutually spaced manner. In this way, it is possible to selectively replace defined sections by auxiliary pads and thus to allow for regeneration of the skin in different areas and use periods.

It is also conceivable that an auxiliary pad is mounted in an overlapping manner over the primary pad, such that the primary pad needs not to be removed and a marginal area of the auxiliary pad adheres to the skin.

BRIEF DESCRIPTION OF THE DRAWINGS

The invention is further elucidated in the following on the basis of embodiment examples shown schematically in the drawings, where.

DESCRIPTION OF THE SELECTED EMBODIMENTS

Figure 1:
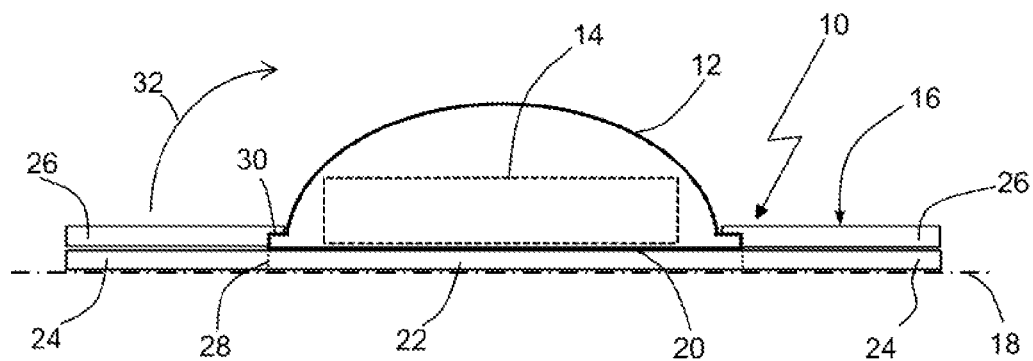
FIG. 1 is a side view of a skin-mountable medical device with a plaster kit for adhesion of a patch portion to the skin.

Referring to the drawings, a medical device 10 worn on the body of a patient for long-term diagnostic or therapeutic applications comprises a patch portion 12, a process unit 14 e.g. formed by a glucose sensor or insulin delivery set and a plaster kit 16 adapted for securing the patch portion on the skin 18 of the patient.

The patch portion 12 has a base including a lower contact surface 20 facing the skin 18 and supporting the process unit 14 preferably as a dimensionally stable platform. The process unit 14 can include an infusion needle projecting through an access port into the skin (not shown). Further details of such infusion devices for continuous glucose control may be found in EP-A 1 923 081, which is incorporated by reference herein. In other applications process unit mounted on the patch portion 12 comprises a sensor or an electronic component such as an RFID-chip.

The contact surface 20 of the patch portion 12 may be joined to the upper side of a central part or base pad 22 of the plaster kit 16 e.g. by means of a structural adhesive. All parts of the plaster kit 16 comprise a carrier layer, i.e. a foil or textile fabric, and a pressure-sensitive adhesive coating which releasably adheres on the skin 18 by applying pressure.

It is also conceivable that a patch portion is construed to adhere directly to the skin 18. For this purpose, the lower surface of the patch may have an adherent coating which is covered by a liner prior to use. Alternatively, an adhesive may be directly applied by means of a dosing device at the time of use.

The plaster kit 16 is specifically designed for a prolonged wearing time on the skin 18. For this purpose, the plaster kit 16 includes a primary pad 24 and at least one auxiliary pad 26. The primary pad 24 is adapted to initially adhere to at least a section of a skin surface in an outer periphery adjacent to the contact surface 20 or the central part 22, respectively. The at least one auxiliary pad 26 is connectable or connected to the patch portion 12 and adapted to replace the primary pad 24 after a given wearing time.

As shown in FIG. 1, the primary pad 24 forms a ring-like slice which is detachable connected to the base pad 22 by means of a circular perforation line 28. In the illustrated initial condition, the primary pad 24 is applied to the skin 18 on one side and carries an auxiliary pad 26 in a layered configuration on the other side. The inner edge of the auxiliary pad 26 is bendably connected to a rim 30 of the patch portion 12 and thereby forms a flap which can be pivoted in direction of arrow 32 to uncover the primary pad 24 for removal.

Figure 2:
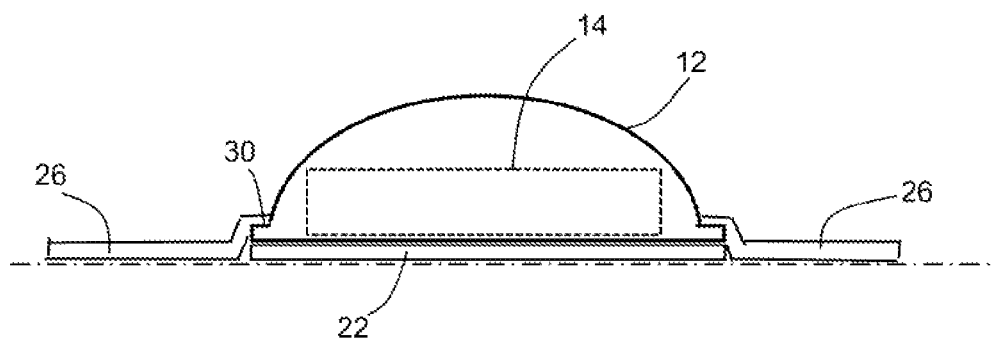
FIG. 2 shows the medical device of FIG. 1 retained with an auxiliary pad of the plaster kit.

As apparent from FIG. 2, when the primary pad is removed, the circumferential border section of the auxiliary pad 26 which protrudes over the rim is swiveled back for attachment to the skin 18. During this exchange procedure, the patch portion 12 remains affixed to the skin 18 by means of the base pad 22.

Figure 3:
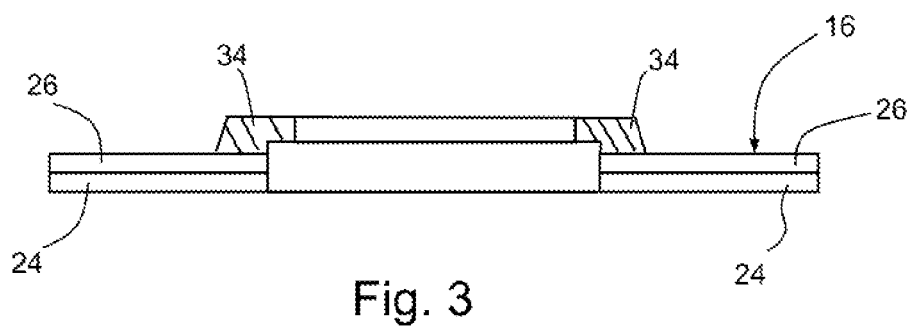
FIG. 3 is a sectional view of a further embodiment of a plaster kit.

FIG. 3 shows a similar embodiment of a plaster kit 16 comprising a stack of an annular primary and auxiliary pad 24, 26. For further improvement, a ring-shaped frame 34 is connected to the inner edge of the auxiliary pad 26. This frame 34 is formed as a molded component and can be engaged to the rim 30 of the patch portion 12 in a form-locking manner.

Figure 4:
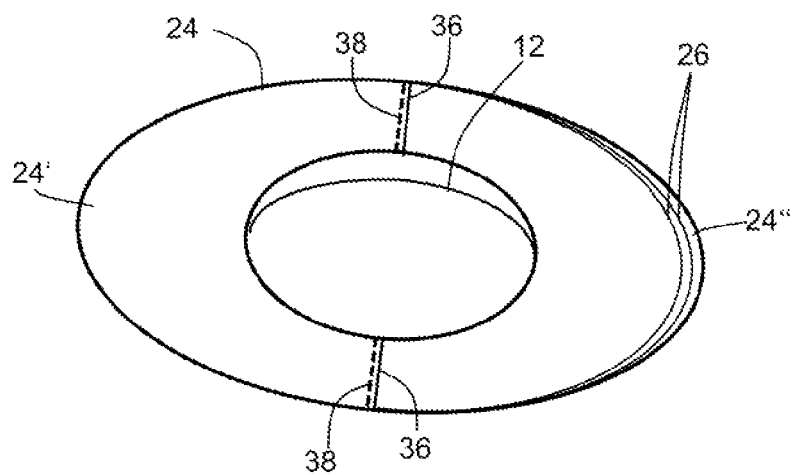
FIGS. 4 and 5 shows the device with a plaster kit comprising a stack of auxiliary pads in a perspective and a side view.

As illustrated in FIG. 4, a further embodiment comprises stack of at least two auxiliary pads 26 which are joined together in a parallel folding pattern similar to Leporello. The auxiliary pads 26 are formed as half-rings which are joined at their ends 36 in a stowable arrangement. On the opposite side, the uncovered half-ring of the primary pad 24 is construed as a tear-off section 24' which can be independently separated from the skin 18. For this purpose, the tear-off section 24' is connected through a pull-linkage 38 to the remaining section 24" of the primary pad 24.

Figure 5:
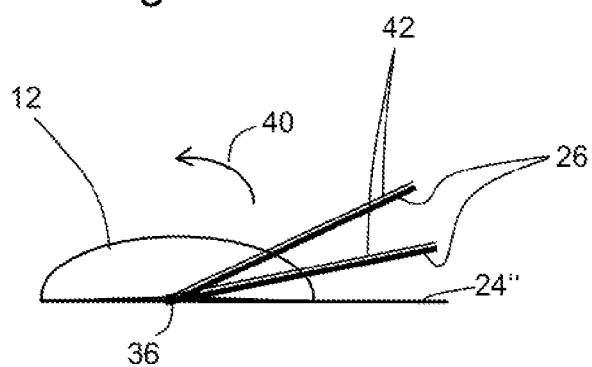

As further illustrated in FIG. 5, the auxiliary pads 26 can be sequentially turned over in the direction of arrow 40 into a functional position adhering to the skin 18. Prior to use, the self-adhesive side of the auxiliary pads 26 is covered by a liner 42 which can be easily removed.

Figure 6:
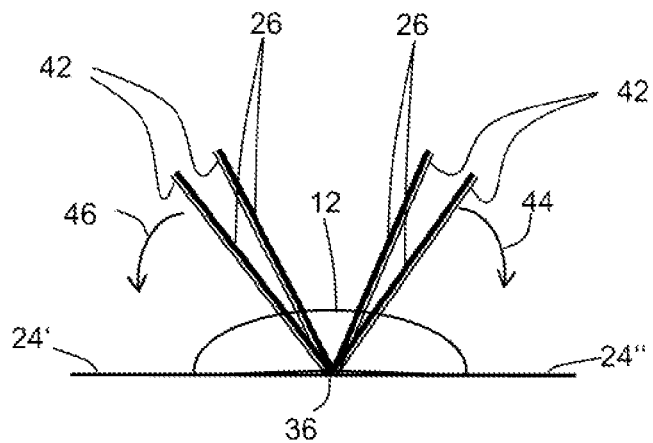
FIG. 6 shows a further assembly of auxiliary pads in a view similar to FIG. 4.

FIG. 6 shows a similar configuration in which two pairs of auxiliary pads 26 are arranged to be folded over in opposite directions 44, 46 to replace the tear-off sections 24', 24" of the primary pad 24.

Figure 7:
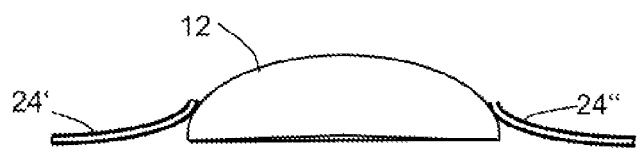
FIGS. 7 and 8 are side and top views of alternate plaster kit with separated tear-off sections.
Figure 8:
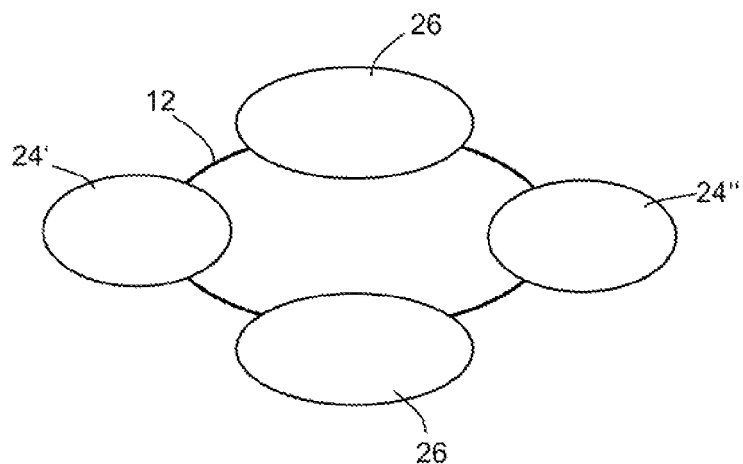

As can be seen from FIGS. 7 and 8, the primary pad may comprise several tear-off sections 24', 24" which are separated from each other in different sectors of the circumference of the patch portion 12. These sections laterally overlap the patch portion 12 and are selectively replaceable as the need arises by auxiliary pads 26. In this case, the auxiliary pads 26 have to be stored as separate items in the initial phase of use.

Figure 9:
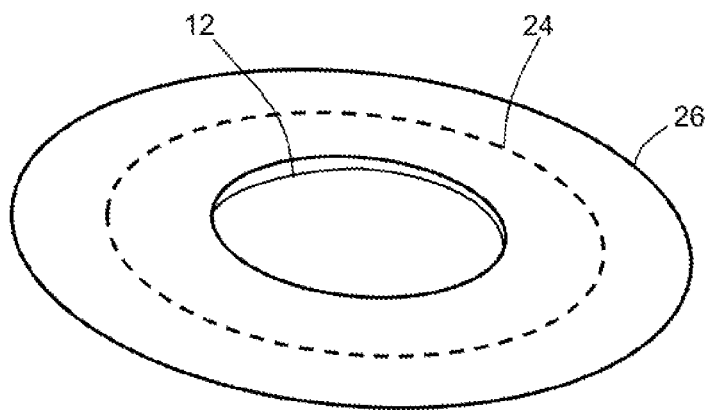
FIG. 9 shows a still further embodiment of a plaster kit with an auxiliary pad in top view.

FIG. 9 exemplifies another embodiment, in which a primary pad 24 is used in an initial phase use for secure fixation of the patch portion 12 to the skin 18. Thereafter an auxiliary pad 26 is mounted in an overlapping manner over the primary pad 24, such that a peripheral area of the auxiliary pad 26 adheres to the skin 18.

The invention claimed is:

1. Skin-mountable medical device, comprising:
    a process unit;
    a patch portion housing the process unit;
    a primary pad extending from the patch portion, the primary pad including
        a primary carrier layer having a tear-off section configured to detach the primary pad from the patch portion, and
        a primary adhesive on the primary carrier layer to releasably adhere to skin; and
    an auxiliary pad layered at least partially over the primary pad, the auxiliary pad being bendably connected to the patch portion for pivoting to uncover the primary pad during removal, the auxiliary pad including
        an auxiliary carrier layer, and
        an auxiliary adhesive on the auxiliary carrier layer to releasably adhere to the skin after removal of the primary pad.

2. Medical device according to claim 1, further comprising:
    a base pad joined to the patch portion and the primary pad, the base pad including
        a base carrier layer, and
        a base adhesive on the base carrier layer to releasably adhere to the skin; and wherein the tear-off section of the primary carrier layer includes a perforation line between the base carrier layer and the primary carrier layer.

3. Skin-mountable medical device, comprising:
a patch portion with a contact surface facing the skin of a patient during use;
a process unit particularly formed by a sensor or medication delivery set attached to the patch portion;
a adhesive kit for securing the patch portion to the skin, wherein the adhesive kit has a primary pad adapted to releasably adhere to at least a section of a peripheral skin surface surrounding the contact surface, characterized in that the adhesive kit further comprises at least one auxiliary pad which is connectable or connected to the patch portion and adapted to functionally replace the primary pad after a wearing time;
wherein the primary pad and the at least one auxiliary pad at least partially overlap one another in a layered configuration;
wherein the primary pad has a tear-off perforation for allowing removal of the primary pad; and
wherein the auxiliary pad is bendably connected to the patch portion and forms a flap to uncover the primary pad for removal.

4. Medical device according to claim 3, wherein an adhesive coating of the auxiliary pad is separated by a liner from the primary pad.

5. Medical device according to claim 3, wherein the adhesive kit further comprises a base pad fixedly connected to the contact surface of the patch portion.

6. Medical device according to claim 3, wherein the auxiliary pad is formed as a separate ring which can be applied over the periphery of the patch portion.

7. Medical device according to claim 3, further comprising a ring-shaped frame which is affixed to the inner edge of an annular auxiliary pad, wherein the frame can be engaged to the patch portion.

8. Medical device according to claim 3, further comprising a stack of at least two auxiliary pads which are joined together in a parallel folding pattern particularly in a Leporello fashion for sequential unfolding into a use position.

9. Medical device according to claim 3, wherein the auxiliary pads each are formed as a half-ring adapted to be turned over into a functional position adhering to the skin.

10. Medical device according to claim 3, wherein the patch portion remains affixed to the skin while the primary pad is replaced.

11. Medical device according to claim 3, wherein the primary pad has a tear-off section which can be independently separated from the skin.

12. Medical device according to claim 11, wherein the tear-off section is connected by means of a pull linkage to a remaining section of the primary pad.

13. Medical device according to claim 3, wherein the primary pad comprises several separate sections in a mutually spaced manner which are selectively replaceable by auxiliary pads.

14. Medical device according to claim 3, wherein an auxiliary pad is mounted in an overlapping manner over the primary pad, such that a marginal area of the auxiliary pad adheres to the skin.

15. Medical device according to claim 3, wherein the primary pad and the at least one auxiliary pad each include a carrier layer and an adhesive coating the carrier layer for releasably adhering to the skin.

16. Medical device according to claim 15, wherein the carrier layer includes a textile fabric.

17. Medical device according to claim 15, wherein the carrier layer includes a foil.

* * * * *